United States Patent [19]

Choy et al.

[11] Patent Number: 5,338,867
[45] Date of Patent: Aug. 16, 1994

[54] PREPARATION OF 4β- AMINO PODOPHYLLOTOXIN COMPOUNDS

[75] Inventors: William Choy; Jen Chen, both of Sunnyvale; Bijan Almassian, Belmont, all of Calif.

[73] Assignee: Genelabs Technologies, Inc., Redwood City, Calif.

[21] Appl. No.: 872,282

[22] Filed: Apr. 24, 1992

[51] Int. Cl.$^5$ .......................................... C07D 307/77
[52] U.S. Cl. ........................................... 549/298
[58] Field of Search ........................................... 549/298

[56] References Cited

U.S. PATENT DOCUMENTS

| | | |
|---|---|---|
| 4,728,740 | 3/1988 | Vyas et al. ............... 549/298 |
| 4,788,216 | 11/1988 | Leander et al. ............ 549/298 |
| 5,057,616 | 10/1991 | Jennings et al. ........... 549/298 |
| 5,106,996 | 4/1992 | Kaneko et al. ............. 549/298 |
| 5,132,322 | 7/1992 | Lee et al. ................. 549/298 |

FOREIGN PATENT DOCUMENTS

| | | |
|---|---|---|
| 0023884 | 2/1988 | Japan . |
| 0093589 | 4/1989 | Japan . |
| 0117885 | 5/1989 | Japan . |
| WO90/09788 | 9/1990 | PCT Int'l Appl. . |

OTHER PUBLICATIONS

Lee, K.-H., et al., "Antitumor Agents. 111. New 4-Hydroxylated and 4-Halogenated Anilino Derivatives of 4'-Demethylepipodophyllotoxin as Potent Inhibitors of Human DNA Topoisomerase II," J. Med. Chem. 33:1364–1368 (1990).

*Primary Examiner*—C. Warren Ivy
*Assistant Examiner*—A. A. Owens
*Attorney, Agent, or Firm*—Peter J. Dehlinger; Vincent M. Powers

[57] ABSTRACT

A method of preparing a 4'-0-demethy-4β-NHR podophyllotoxin, where R is an aryl or dialkyl amino alkyl group, is disclosed. The method includes reacting $H_2NR$ under basic conditions with a mixture of α and β epimers of 4'-0-demethyl-4-bromo-podophyllotoxin, to form an epimeric mixture of the 4'-0-demethyl-4-NHR-podophyllotoxin compounds, removing acidic impurities which bind to silica gel in a dichloromethane solvent, and crystallizing 4'-0-demethyl-4β-NHR-podophyllotoxin from its α epimer.

5 Claims, 2 Drawing Sheets

PREPARATION OF 4β- AMINO PODOPHYLLOTOXIN COMPOUNDS

FIELD OF THE INVENTION

The present invention relates to novel 4β-amino podophyllotoxin compounds useful in the treatment of tumors, and to methods of synthesis of the compounds.

BACKGROUND OF THE INVENTION

A class of amine derivatives, particularly aryl amine derivatives, of 4'-demethylepipodophyllotoxin compounds useful as anti-tumor agents has been described (see, for example, Lee, K.-H., et al., J Med Chem, 33:1364 (1990), and Lee, K.-H., et al., PCT patent application WO 90/09788).

The published syntheses of these compounds involves forming a mixture of α and β epimers of 4'-O-demethyl-4-bromo-podophyllotoxin (4'-O-demethyl-4-bromo-desoxypodophyllotoxin), and reacting the mixture of epimers with a suitable amine, forming an epimeric mixture of the 4'-O-demethyl-4-amine-podophyllotoxin (4'-O-demethyl-4-amine-desoxypodophyllotoxin). The α and β epimeric products are separated by chromatography. This method is suboptimal for large-scale production of the desired 4'-O-demethyl-4β-amine-podophyllotoxin (4'-O-demethyl-4β-amine-desoxypodophyllotoxin), because of the need for chromatographic separation of products.

SUMMARY OF THE INVENTION

The method of the invention is designed for efficient, large-scale production of 4'-O-demethy-4β-NHR-podophyllotoxin (4'-O-demethy-4β-NHR-desoxypodophyllotoxin), where R is an aryl or dialkylaminoalkyl group. The method includes reacting H$_2$NR under basic conditions with the α and β epimers of 4'-O-demethyl-4-bromo-podophyllotoxin (4'-O-demethyl-4-bromo-desoxypodophyllotoxin), to form an epimeric mixture of the 4'-O-demethyl-4-NHR-podophyllotoxin compounds, removing acidic impurities which bind to silica gel in a dichloromethane solvent, and crystallizing 4'-O-demethyl-4β-NHR-podophyllotoxin from its α epimer.

In one embodiment, the NHR group is 4-nitroaniline or 4-fluoroaniline, and the crystallizing step includes dissolving the epimer mixture in a lower haloalkane/lower alkanol solvent mixture, such as a dichlormethane/methanol, and distilling the mixture until the ratio of the solvent components is such as to cause the 4'-O-demethyl-4β-NHR-podophyllotoxin to crystallize out of the mixture.

Also disclosed are novel 4'-O-demethyl-4β-NHR-podophyllotoxin compounds in which NHR is an alkyl amine of the form NH—(CH$_2$)$_n$—NR$_1$R$_2$, where R$_1$ and R$_2$ are hydrogen or lower alkyl groups, and n=2–4.

These and other objects and features of the invention will become more fully apparent when the following detailed description of the invention is read in conjunction with the figures, wherein:

DETAILED DESCRIPTION OF THE INVENTION

Figure 1A:
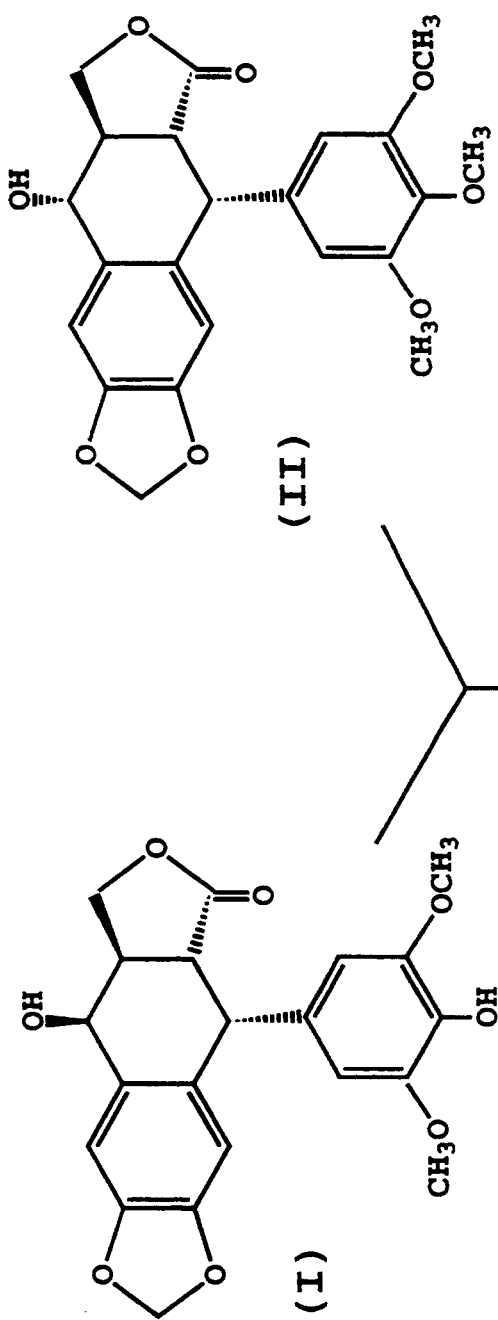
FIGS. 1A and 1B illustrate the bromination of podophyllotoxin (1B) or 4'-O-demethyl-4-epipodophyllotoxin (1A) to form an epimeric mixture of 4'-O-demethyl-4-bromo-podophyllotoxin.
Figure 1B:
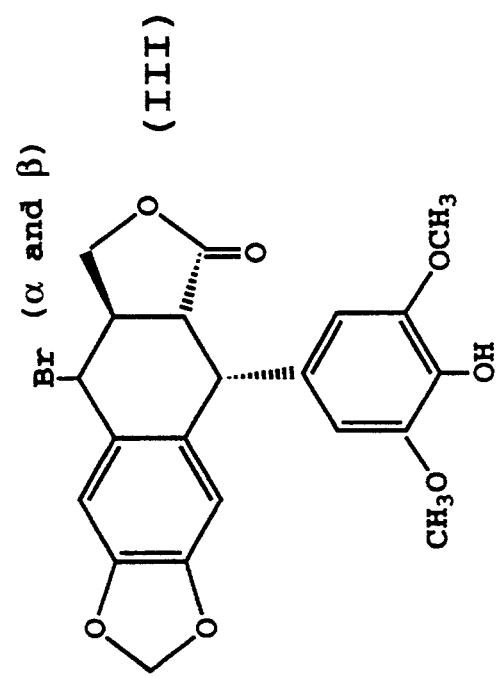

The method of the invention will be described with respect to the following reaction steps:

Step 1: Reacting H$_2$NR under basic conditions with a mixture of α and β epimers of 4'-O-demethyl-4-bromo-podophyllotoxin. In one general embodiment, illustrated in FIG. 1B, the mixture of α and β epimers (compound III) is formed by reacting podophyllotoxin (compound II) with HBr over an extended time period, as detailed in Examples 1 and 2. In a second general embodiment, 4'-O-demethyl-4-epipodophyllotoxin (compound I) (or a mixture of 4'-O-demethyl-4α-podophyllotoxin and 4'-O-demethyl-4β-podophyllotox) is reacted with HBr gas under similar conditions, but for a relatively short time period, e.g., 1 hour.

Figure 2:
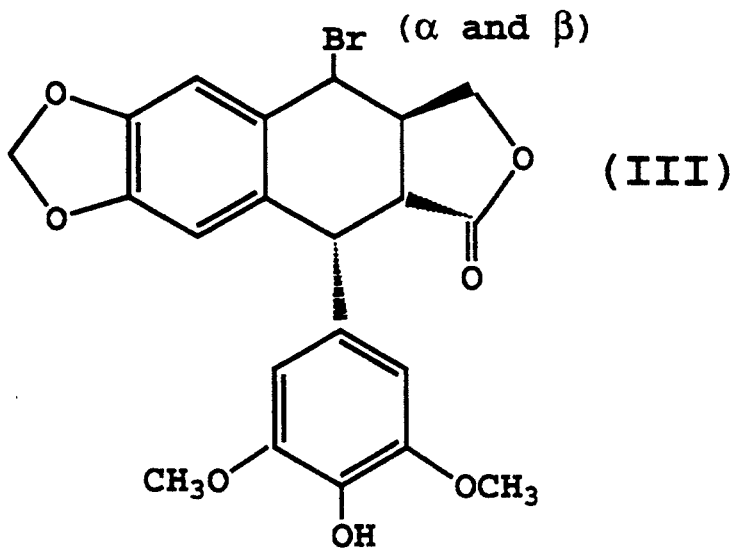
FIG. 2 illustrates the reaction of an NH$_2$R anilino compound with the epimers of 4'-O-demethyl-4-bromo-podophyllotoxin, to form an epimeric mixture of 4'-O-demethyl-4-NHR-podophyllotoxin.
Figure 2:
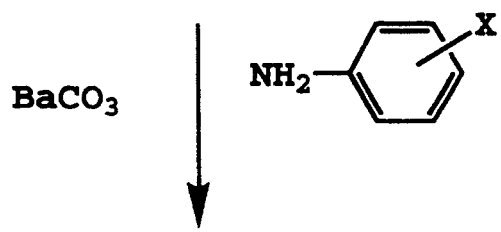
Figure 2:
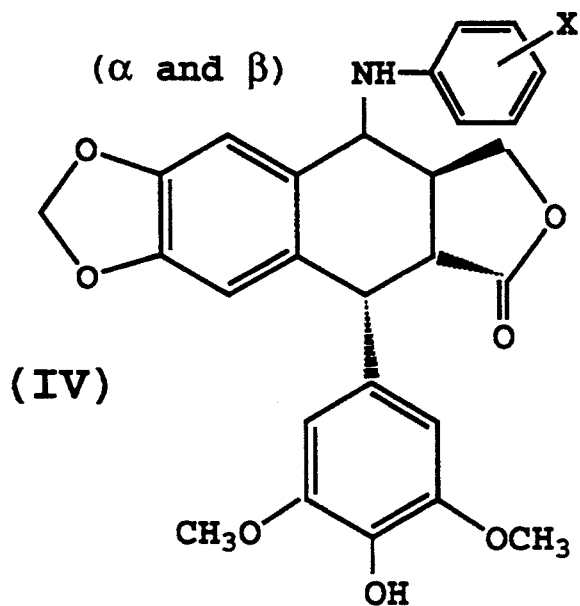

The H$_2$NR compound may be an anilino compound, preferably an anilino compound substituted at one or more positions with a halide, amine, monoalkyl amine, dialkylamine, nitro, acid, or ester of a lower alkyl group, and most preferably where the substitution occurs at the para position of the aniline ring. Exemplary anilino compounds are as 4-nitroaniline, 4-flouroaniline, 4-ethoxycarbonyl, forming corresponding α and β epimers of 4'-O-demethyl-4-anilino-podophyllotoxin, such as 4'-O-demethyl-4-(4''-fluoroanilino)-podophyllotoxin and 4'-O-demethyl-4-(4''-nitroanilino-podophyllotoxin, as illustrated in FIG. 2, and as detailed in Examples 1 and 2, respectively.

Alternatively, the H$_2$NR compound may be an alkyl diamine of the form NH$_2$—(CH$_2$)$_n$—NR$_1$R$_2$, where n is 2–4, and R$_1$ and R$_2$ are hydrogen or lower alkyl groups, meaning 1–4 carbon alkyl groups.

Step 2: Removing from the second mixture, acidic impurities which bind to silica gel in a dichloromethane solvent, yielding a purified mixture containing the 4'-O-demethyl-4-NHR-podophyllotoxin α and β epimers.

According to one feature of the invention, it has been found that removal of the acidic impurities prevents undesired side reactions which can occur during product crystallization. The step of removing acidic impurities is preferably carried out by passing the reaction mixture from Step 1 over a silica gel column, and eluting the column with dichloromethane, as detailed in Examples 1 and 2. Other solvents effective to remove acid impurities which are retained in the silica gel/dichloromethane system may also be employed. The eluant may be concentrated, e.g., under vacuum.

Step 3: Crystallizing 4'-O-demethyl-4β-NHR-podophyllotoxin from its α epimer in the purified mixture.

According to another aspect of the invention, it has been found that the desired 4'-O-demethyl-4β-NHR-podophyllotoxin product can be obtained in pure form from the purified epimer mixture from Step 1 and 2 by crystallization. In a preferred method, the purified epimer mixture from Step 2 is first dissolved in a lower haloalkane, i.e., a halogenated lower alkane having 1–4 carbon atoms. Exemplary lower haloalkanes in dichloromethane, chloroform, 1,2-dichloroethane, and Cl$_2$CHCHCl$_2$. To the solution of epimers is added a lower alkanol, meaning a 1–4 carbon alcohol, such as methanol, ethanol, propanol, isopropanol or butanol. Preferably the lower alkanol is added to the solution of epimers during heating, with the alkanol being added at a rate which maintains a constant solvent volume as most of the original solvent, e.g., lower haloalkane, is removed by distillation. After addition of the lower alkanol, distillation is continued until crystallization of the 4'-0-demethyl-4β-NHR-podophyllotoxin from its α epimer occurs. Typically, the crystallized material is recrystallized one or more times.

The following examples illustrate the method of the invention for use in forming to preferred 4'Demethyl-4β-(4"-anilino)-4-desoxypodophyllotoxin compounds.

EXAMPLE 1

Preparation of 4'Demethyl-4β(4"-fluoroanilino) -4-desoxypodophyllotoxin

Under argon atmosphere and into a 3 necked flask fitted with rubber stoppers, inserted thermometer, mechanical stirrer, and an inlets for HBr, was placed podophyllotoxin (1.4 kg) and dry 1,2 dichloroethane (17.6 kg). To the resulting solution was added anhydrous ether (1.4L). The reaction mixture was cooled to 5° C. in an ice bath. HBr (2.92 kg) was slowly bubbled into the solution at such a rate so that the reaction temp was <10° C. The entire flask was stored overnight in a 5° C. cold room. Anhydrous $Na_2SO_4$ (1.4 kg, powder) was added and then the entire reaction mix was quickly filtered through a fritted disk funnel 30 minutes later. The solids were rinsed with $CH_2Cl_2$ (1L) and filtered.

The combined filtrate was purged with a stream of argon for 30 minutes and then concentrated on a rotary evaporator. Three times the residue was diluted with $CH_2Cl_2$ (3L) and evaporated. The resulting foam was quickly dissolved into dry 1,2 dichloroethane (17.6 kg) under Ar and then powdered $BaCO_3$ (1.62 kg) was added with mechanical stirring. After cooling to <5° C., 4-fluoroaniline (770 g) was added dropwise over 30 minutes into the resulting stirred suspension. After overnight stirring at 5° C., the reaction mix was filtered through a fritted disk funnel containing Celite (600 g) and the solids rinsed twice with $CH_2Cl_2$ (2L each). The combined filtrate was extracted with $H_2O$ (5L each) and once with saturated aqueous NaCl solution (5L). After drying over anhydrous $Na_2SO_4$ (1 kg), the organic phase was filtered and then concentrated on a rotary evaporator. The residue was diluted with $CH_2Cl_2$ (4.5L) and filtered through a silica gel column (640 g). After further elution of the column with $CH_2Cl_2$ (2L), the combined eluants were concentrated using a rotary evaporator.

The residue was diluted with $CH_2Cl_2$ (2.8L) and filtered through a silica gel (5 kg) column. Using $CH_2Cl_2$ as eluent, collect and discard the first 8L of filtrate. Collect and concentrate in vacuo, using a rotary evaporator, the next 23L of filtrate from the column. Add MeOH (3.4L) to induce crystallization from the residue and stored overnight in a <5° C. cold room. After suction filtration the solid was dissolved in hot $CH_2Cl_2$ (4 ml/mg of solid) and allowed to cool to room temperature. After another filtration, MeOH (4 ml/mg of solid used in the above hot $CH_2Cl_2$ step) was added at such a rate as to maintain a constant volume during the distillation of the filtrate. Distillation continued until small white prisms began to recrystallize out and then the suspension was allowed to cool to <5° C.

After overnight storage in a <5° C. cold room, the solid was filtered and washed with several small portions of ice cold MeOH. After the above, recrystallization was repeated. The yield of isolated product after drying in vacuo at 0° C. was 321 g and has the following characteristics: mP:203.5–5° C.;$[α]^{24}_D = -120°$ (c=7.5 mg/ml, $CHCl_3$).

EXAMPLE 2

Preparation of 4'-Demethyl-4β-(4"-nitroanilino)-4-desoxypodophyllotoxin

Under argon atmosphere and into a 3 necked flask fitted with rubber stoppers, inserted thermometer, mechanical stirrer, and an inlet for HBr was placed podophyllotoxin (1.5 kg) and dry 1,2 dichloroethane (18.84 kg). To the resulting solution was added anhydrous ether (1.5L). The reaction mixture was cooled to <5° C. in an ice bath. HBr (3 kg) was slowly bubbled into the solution at such a rate so that the reaction temp was <10° C. The entire flask was stored overnight in a <5° C. cold room. Anhydrous $Na_2SO_4$ (1.51 kg, powder) was added and then the entire reaction mix was quickly filtered through a fritted disk funnel 30 minutes later. The solids were rinsed twice with 500 ml portions of $CH_2Cl_2$ and filtered.

The combined filtrate was purged with a stream of argon for 30 minutes and then concentrated on a rotary evaporator. Thrice, the residue was diluted with $CH_2Cl_2$ (3L) and evaporated. The resulting foam was quickly dissolved into dry 1,2 dichloroethane (19 kg) under Ar and then powdered $BaCO_3$ (1.74 kg) was added with mechanical stirring. After cooling to <5° C., 4-nitroaniline (900 g) dissolved into dry acetonitrile (11.S kg) was added dropwise over 120 minutes into the resulting stirred suspension.

After overnight stirring at <5° C., the reaction mix was filtered through a fritted disk funnel containing a bed of Celite (275 g) and the solids rinsed twice with $CH_2Cl_2$ (1L each). The combined filtrate was extracted twice with $H_2O$ (1.5L each) and once with saturated aqueous NaCl solution (500 ml). After drying over anhydrous $Na_2SO_4$ (1.59 kg), the organic phase was filtered and then concentrated on a rotary evaporator. The residue was diluted with $CH_2Cl_2$ (24L) and filtered through a silica gel column (400 g). After further elution of the column with $CH_2Cl_2$ (3L), the combined eluents were concentrated to 5L using a rotary evaporator.

Isopropanol (20L) was added and the resulting solution distilled until the pot temperature reached 67° C. After cooling to room temperature, the resulting solids were filtered. Additions of $CH_2Cl_2$ (5L) and then isopropanol (17.5L) followed by distillation described above provided another solid after cooling to room temperature and filtering. After adding warm $CH_2Cl_2$ (50 ml/g of solid) and filtering, MeOH (30 ml/g of solid) was added at such a rate so as to maintain a constant volume during distillation of the filtrate. Distillation was then continued until yellow small needles began to recrystallize out. The suspension was allowed to cool to 25° C. and the solids were then filtered. Recrystallizations using the above $CH_2Cl_2$/MeOH protocol were repeated twice. The yield of isolated product after drying in vacuo at 60° C. was 255 g and has the following characteristics:

mP:248.5–250.5° C.;$[α]^{25}_D = -181.7°$ (c=4.1 mg/ml, $CHCl_3$).

It is claimed:

1. A method of preparing a 4'-0-demethyl-4β-NHR podophyllotoxin compound of the form:

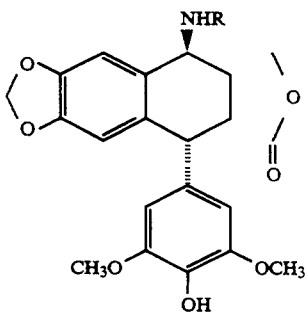

wherein NHR has the form:
(a)

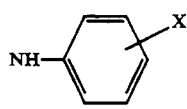

or (b) NH—(CH$_2$)$_n$—NR$_1$R$_2$, where X is a radical selected from the group consisting of a halide, amine, monoalkyl amine, dialkylamine, nitro, acid, or ester of a lower alkyl group, R$_1$, R$_2$ are hydrogen or lower alkyl groups, and n=2–4, said method comprising:

reacting a mixture of α and β epimers of 4'-O-demethyl-4-bromo-podophyllotoxin with H$_2$NR under basic conditions, to form a second mixture of α and β epimers of 4'-O-demethyl-4-NHR-podophyllotoxin, and acidic reactionproduct impurities, removing from the second mixture, acidic impurities which bind to silica gel in a dichloromethane solvent, yielding a purified mixture of the 4'-O-demethyl-4-NHR-podophyllotoxin α and β epimers, and crystallizing 4'-O-demethyl-4β-NHR-podophyllotoxin from its α epimer in the purified mixture.

2. The method of claim 1, wherein the purified mixture contains at least about 5 g of 4'-O-demethyl-4β-NHR-podophyllotoxin.

3. The method of claim 1, wherein NHR is 4-nitroaniline or 4-fluoroaniline, and said crystallizing includes dissolving the purified mixture in a lower haloalkane/lower alkanol solvent mixture, and distilling the mixture until the ratio of the solvent components is such as to cause the 4'-O-demethyl-4β-NHR-podophyllotoxin to crystallize out of the mixture.

4. The method of claim 3, wherein the solvent mixture is a dichloromethane/methanol mixture.

5. The method of claim 1, wherein NHR has the form:

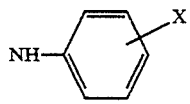

* * * * *

UNITED STATES PATENT AND TRADEMARK OFFICE
CERTIFICATE OF CORRECTION

PATENT NO. : 5,338,867
DATED : Aug. 16, 1994
INVENTOR(S) : William Choy, Jen Chen and Bijan Almassian It is certified that error appears in the above-identified patent and that said Letters Patent is hereby corrected as shown below:

In claim 1, at column 5, lines 1-13, the captioned structure is replaced with the following:

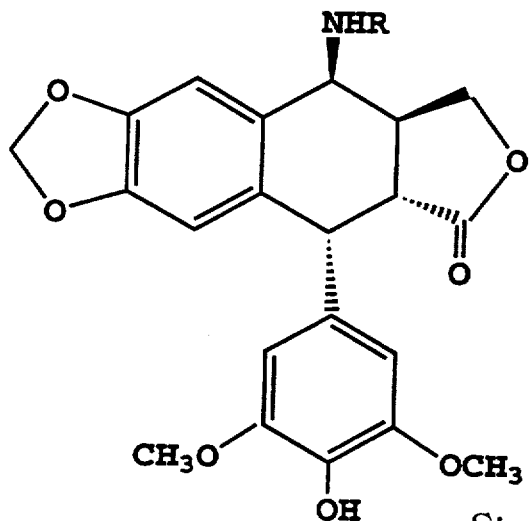

Signed and Sealed this

Nineteenth Day of September, 1995

Attest:

BRUCE LEHMAN

Attesting Officer          Commissioner of Patents and Trademarks